United States Patent [19]
Roe et al.

[11] Patent Number: 6,090,090
[45] Date of Patent: Jul. 18, 2000

[54] DIAPER INSERT HAVING ADJUSTABLE ABSORBENT ASSEMBLIES

[75] Inventors: Donald C. Roe, West Chester; Carl L. Bergman, Loveland, both of Ohio

[73] Assignee: The Procter & Gamble Company, Cincinnati, Ohio

[21] Appl. No.: 09/234,360

[22] Filed: Jan. 20, 1999

Related U.S. Application Data

[63] Continuation-in-part of application No. 08/925,965, Sep. 9, 1997, Pat. No. 5,968,028, which is a continuation-in-part of application No. 08/686,290, Jul. 25, 1996, Pat. No. 5,716,351.

[51] Int. Cl.[7] ........................................... A61F 13/15
[52] U.S. Cl. ............................................. 604/385.1
[58] Field of Search ............................. 604/385.1, 385.2, 604/386, 391

Primary Examiner—Wynn Wood Coggins
Assistant Examiner—A. T. Nguyen
Attorney, Agent, or Firm—David M. Weirich; Steven W. Miller; Jacobus C. Rasser

[57] ABSTRACT

An absorbent insert for use with an outer cover, the outer cover having a front waist region, a rear waist region, a longitudinal centerline and a lateral centerline perpendicular to said longitudinal centerline. The absorbent insert includes a first absorbent assembly; a second absorbent assembly; and an adjustment member adjustably joining the first absorbent assembly and the second absorbent assembly such that the first absorbent assembly and the second absorbent assembly are moveable relative to each other in at least a direction parallel to said longitudinal centerline. The insert also includes a slip element joined with at least a portion of the first absorbent assembly, the slip element providing a low friction surface such that at least a portion of the first absorbent assembly can be positioned over at least a portion of the second absorbent assembly in an overlapping configuration.

13 Claims, 6 Drawing Sheets

DIAPER INSERT HAVING ADJUSTABLE ABSORBENT ASSEMBLIES

This is a CIP of Ser. No. 08/925,965 filed Sep. 9, 1997 now U.S. Pat. No. 5,968,028, which is a CIP of Ser. No. 08/686,290 filed Jul. 25, 1996 now U.S. Pat. No. 5,716,351.

FIELD OF THE INVENTION

The present invention relates to articles which absorb and/or contain bodily exudates, including disposable absorbent articles such as diapers, adult incontinence products, sanitary napkins and the like. More particularly, the invention relates to disposable absorbent articles having adjustable absorbent assemblies which provide improved fit and containment characteristics.

BACKGROUND OF THE INVENTION

The major function of absorbent articles such as disposable diapers and adult incontinence briefs, is to absorb and contain body exudates. Such articles are also intended to prevent body exudates from soiling, wetting, or otherwise contaminating clothing or other articles, such as bedding, that come in contact with the wearer. Disposable diapers, such as those disclosed in U.S. Pat. No. 3,860,003 issued to Kenneth Barclay Buell on Jan. 14, 1975, generally have a topsheet, a backsheet, and an absorbent core. However, despite the effectiveness of such structures, body exudates often leak or are stored in the diaper in such a way that the exudates may irritate the skin of the wearer. Although it is generally known that urine and feces (BM) have significantly different physical properties and forms, current diapers do not have distinct zones configured for the collection and processing of urine and feces (BM).

While attempts have been made to separate the wastes by incorporating various fecal barriers into diapers, these attempts suffer because a single, nonadjustable absorbent assembly is used to collect both urine and BM. Since humans vary considerably in terms of size and dimensions even within a given weight range, (for example, the distance between the urethra and anus), it has been found to be advantageous to provide urine and BM collection zones with separate absorbent assemblies which are adjustable relative to each other.

Thus, it may be desirable to provide a diaper having an adjustable chassis. Further, it may be desirable to provide a diaper or insert having separate urine and feces (BM) collection zones. It may also be advantageous to provide a diaper or insert having separate urine and feces collection zones having separate absorbent assemblies wherein the relative spacing between the absorbent assemblies is adjustable or wherein the relative position of the absorbent assemblies relative to the body of the wearer is adjustable. A still further advantage the present invention is to provide an adjustment member joined to the separate absorbent assemblies which is elastically adjustable. Finally, it may be advantageous to provide an adjustment member joined to the separate absorbent assemblies which is inelastically adjustable, inelastically adjustable, or reversibly adjustable.

SUMMARY OF THE INVENTION

In order to overcome the deficiencies of the prior art, the present invention provides an absorbent insert for use with an outer cover, the outer cover having a front waist region, a rear waist region, a longitudinal centerline and a lateral centerline perpendicular to said longitudinal centerline. The absorbent insert includes a first absorbent assembly; a second absorbent assembly; and an adjustment member adjustably joining the first absorbent assembly and the second absorbent assembly such that the first absorbent assembly and the second absorbent assembly are moveable relative to each other in at least a direction parallel to said longitudinal centerline. The insert also includes a slip element joined with at least a portion of the first absorbent assembly, the slip element providing a low friction surface such that at least a portion of the first absorbent assembly can be positioned over at least a portion of the second absorbent assembly in an overlapping configuration.

BRIEF DESCRIPTION OF THE DRAWINGS

While the specification concludes with claims particularly pointing out and distinctly claiming the subject matter which is regarded as the present invention, it is believed that the description will be better understood from the following descriptions which are taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper.) A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, absorbent inserts, diaper holders and liners, feminine hygiene garments, and the like.

Figure 1:
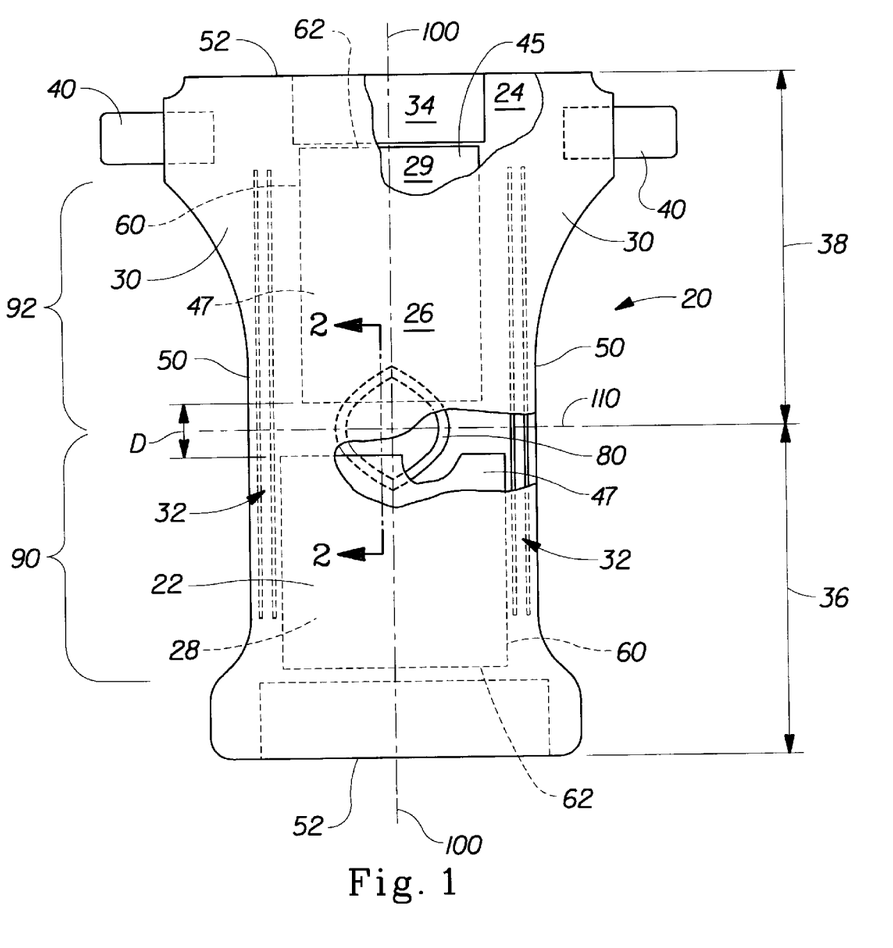
FIG. 1 is a plan view of an absorbent article embodiment of the present invention having portions cut away to reveal the underlying structure, the garment-facing surface of the diaper facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces away from the wearer oriented towards the viewer. As shown in FIG. 1, the diaper 20 preferably comprises a liquid pervious topsheet 24; a liquid impervious backsheet 26 joined with the topsheet 24; a first absorbent assembly 28, a second absorbent assembly 29, each of which is preferably positioned between the topsheet 24 and the backsheet 26; side panels 30; elasticized leg cuffs 32; an elastic waist feature 34; and a fastening system generally designated 40. The diaper 20 is shown in FIG. 1 to have a front waist region 36, a rear waist region 38 opposed to the front waist region 36 and a periphery which is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

FIG. 1 shows a preferred embodiment of the diaper 20 in which the topsheet 24 and the backsheet 26 have length and width dimensions generally larger than those of the first and second absorbent assemblies 28 and 29. The topsheet 24 and the backsheet 26 preferably extend beyond the edges of the first and second absorbent assemblies 28 and 29 to thereby form the periphery of the diaper 20. The chassis 22 of the diaper 20 comprises the main body of the diaper 20. The chassis 22 comprises at least one absorbent assembly and preferably an outer covering layer comprising the topsheet 24 and the backsheet 26. When the absorbent article comprises a separate holder and a liner, the chassis 22 generally comprises the holder and the liner. (For example, the holder comprises one or more layers of material to form the outer cover of the article and the liner comprises an absorbent composite such as the topsheet, backsheet, and absorbent assemblies. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the chassis 22 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993; each of which is incorporated herein by reference.

Figure 2:
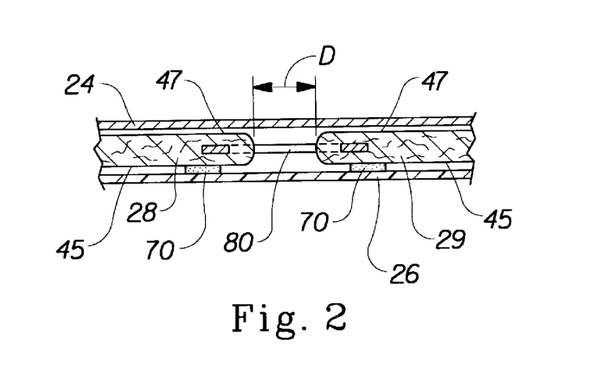
FIG. 2 is an enlarged fragmentary cross-sectional view taken along section line 2—2 of FIG. 1.

FIG. 2 is a fragmentary cross-sectional view of the diaper 20 taken along section line 2—2 of FIG. 1. As shown in FIG. 2, one embodiment of the diaper 20 of the present invention includes a first absorbent assembly 28 and a second absorbent assembly 29 adjustably joined by the adjustment member 80. (As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.). As shown in FIG. 1, the absorbent assemblies 28 and 29 have longitudinal edges 60, a garment surface 45 and a body surface 47.

In preferred embodiments the backsheet 26 is impervious to liquids (e.g., urine) and comprises a thin plastic film, although other flexible liquid impervious materials may also be used. (The term "flexible" as used herein to refer to films and other suitable backsheet materials refers to materials which are compliant and will readily conform to the general shape and contours of the human body.) The backsheet 26 generally prevents the exudates absorbed and contained in the absorbent assemblies 28 and 29 from wetting articles which contact the diaper 20 such as bedsheets and undergarments. Thus, the backsheet 26 may comprise a woven or nonwoven material, polymeric films such as thermoplastic films of polyethylene or polypropylene, or composite materials such as a film-coated nonwoven material. Preferably, the backsheet is a thermoplastic film having a thickness of about 0.012 mm (0.5 mil) to about 0.051 mm (2.0 mils). Particularly preferred materials for the backsheet include blown films and cast films as manufactured by Tredegar Industries, Inc. of Terre Haute, Ind., under the trade names RR8220 and RR5475, respectively. The backsheet 26 may be embossed and/or matte finished to provide a more cloth like appearance. Further, the backsheet 26 preferably permits vapors to escape from the diaper 20 while still preventing exudates from passing through the backsheet 26 (i.e., backsheet is breathable).

The backsheet 26, or any portion thereof, may be elastically extensible in one or more directions. In one embodiment, the backsheet 26 may comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. Preferably, of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 is generally positioned adjacent at least a portion of the garment surface 45 of the absorbent assemblies and is preferably joined thereto by attachment means 70 such as those well known in the art. For example, the backsheet 26 may be secured to one or more of the absorbent assemblies by a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. More preferably the attachment means will include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minn. and marketed as HL-1258. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body surface 47 of the absorbent assemblies and is preferably joined thereto and to the backsheet 26 by attachment means such as those well known in the art (not shown). Suitable attachment means are described with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 is preferably compliant, soft feeling, and non-irritating to the wearer's skin. Further, the topsheet 24 is preferably liquid pervious, permitting liquids (e.g., urine) to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of a hydrophobic material to isolate the wearer's skin from liquids contained in the absorbent assemblies. There are a number of manufacturing techniques which may be used to manufacture the topsheet 24. For example, the topsheet 24 may be a nonwoven web of fibers spunbond, carded, wet-laid, meltblown, hydroentangled, combinations of the above, or the like. One preferred topsheet 24 comprises a web of staple length polypropylene fibers such as is manufactured by Veratec, Inc., a Division of International Paper Company, of Walpole, Mass. under the designation P-8.

The diaper 20 preferably further comprises at least one elastic waist feature 34 that helps to provide improved fit and containment. The elastic waist feature 34 is intended to elastically expand and contract to dynamically fit the wearer's waist. The elastic waist feature 34 preferably extends at least longitudinally outwardly from at least the waist edge 62 of one of the absorbent assemblies and generally forms at least a portion of the end edge 52 of the diaper 20. However, disposable diapers are generally constructed so as to have two elastic waist features, one positioned in the front waist region 36 and one positioned in the rear waist region 38. Further, while the elastic waist feature 34 or any of its constituent elements can comprise a separate element affixed to the diaper 20, the elastic waist feature 34 is preferably constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985 and the above referenced U.S. Pat. No 5,151,092 issued to Buell on Sep. 9, 1992; and U.S. Pat. No. 5,221,274 issued to Buell on Jun. 22, 1993; each of these references being incorporated herein by reference.

The diaper 20 preferably also comprises a fastening system 40. The fastening system 40 preferably maintains the front waist region 36 and the rear waist region 38 in an overlapping configuration so as to provide lateral tensions about the circumference of the diaper 20 to hold the diaper 20 on the wearer. The fastening system 40 preferably comprises tape tabs and/or hook and loop fastening components although any other known means are generally acceptable. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No. 4,662,875 entitled "Absorbent Article" issued to Hirotsu et al. on May 5, 1987; and the herein before referenced U.S. Pat. No. 5,151,092 issued to Buell on Sep. 9, 1992; and U.S. Pat. No. 5,221,274 issued to Buell on Jun. 22, 1993; each of which is incorporated herein by reference.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application (asymmetrically), the diaper 20 will "self-adjust" during wear.

While the diaper 20 of the present invention preferably has the side panels 30 disposed in the rear waist region 38;

the diaper 20 may be provided with side panels 30 disposed in the front waist region 36 or in both the front waist region 36 and the rear waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. patent application Ser. No. 08/155,048 entitled "Absorbent Article With Multi-Directional Extensible Side Panels" filed Nov. 19, 1993 in the names of Robles, et al.; each of which are incorporated herein by reference.

The diaper 20 preferably further comprises leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff.

In preferred embodiments, the leg cuffs 32 extend generally longitudinally from the front waist region 36 through the crotch region 37 to the rear waist region 38. Although the cuffs 32 may extend from one end edge 52 of the diaper 20 to the opposite end edge 52, it is not necessary that they do so. Further, although the cuffs 32 are preferably structurally mirror images of each other, the cuffs 32 may be configured differently. In any case, preferably the leg cuffs 32 extend laterally outwardly from the longitudinal edges 60 of the absorbent assemblies 28 and 29.

The diaper 20 preferably has a urine collection zone 90 and a feces collection zone 92. The urine collection zone 90 is that portion of the diaper intended to collect and contain the majority of urine deposited into the diaper 20. (However, embodiments are also known in which the urine collection zone 90 collects BM or less than a majority of the urine.) Thus, the urine collection zone 90 is generally located in the front waist region 36 and is generally coordinated with the location of the opening to the urethra. However, the urine collection zone 90 may comprise any portion of the front waist region 36 or the rear waist region 38 of the diaper 20. The urine collection zone 90 may be detachably affixed to the chassis 22 of the diaper 20 and may be constructed using flushable materials. In preferred embodiments, the urine collection zone 90 preferably comprises at least a portion of the first absorbent assembly 28.

The feces collection zone 92 is that portion of the diaper 20 intended to collect and contain the majority of feces deposited into the diaper 20. (However, embodiments are also known in which the feces collection zone collects urine or less than a majority of the feces.) Thus, the feces collection zone 92 is generally located in the rear waist region 38 and is generally coordinated with the location of the opening to the anus. However, the feces collection zone 92 may comprise any portion of the rear waist region 38 or the front waist region 36 of the diaper 20. In preferred embodiments, the feces collection zone 92 preferably comprises at least a portion of the second absorbent assembly 29.

The feces collection zone 92 may comprise similar materials and construction as the urine collection zone 90. Alternately, the feces collection zone 92 may comprise a design and/or materials specific to the processing or storage of feces. For example, if the feces collection zone 92 is intended to absorb low viscosity feces (e.g., from a breast-fed infant) the diaper 20 may comprise a topsheet 26 having one or more apertures in at least the feces collection zone 92. If, on the other hand, more highly viscous feces are to be stored, features having sufficient open void volume may be employed in this zone. The feces collection zone 92 may be detachably affixed to the chassis 22 of the diaper 20 and may be constructed using flushable materials. Exemplary absorbent cores and other structures for collection of feces are described in detail in U.S. Pat. No. 5,342,338 entitled "Disposable Absorbent Article For Low-Viscosity Fecal Material" issued to Roe on Aug. 30, 1994, which is hereby incorporated by reference herein.

The diaper 20 may also comprise pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; PCT Application WO 96/07382 published Mar. 14, 1996, entitled "Absorbent Article Having Pocket Cuff With An Apex"; and PCT Application WO 93/25172 published Dec. 3, 1993, entitled "Spacers For Use In Hygienic Absorbent Articles And Disposable Absorbent Articles Having Such Spacer". Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. An example of a diaper having a transverse barrier is described in PCT Application WO 94/14395, published Jul. 7, 1994, entitled "Absorbent Article Having An Upstanding Transverse Partition". Each of these references is hereby incorporated by reference herein.

The absorbent assemblies 28 and 29 may comprise any absorbent means which is generally compressible, conformable, non-irritating to the wearer's skin, and capable of absorbing and retaining liquids such as urine and other certain body exudates The absorbent assemblies may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent assemblies may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent assemblies should be compatible with the design loading and the intended use of the diaper 20.

The first and second absorbent assemblies 28 and 29 may comprise the same general materials and construction, or may be designed differently. For example, a preferred absorbent assembly for the collection of urine is specifically configured so as to best absorb and contain urine whereas a preferred absorbent assembly for the collection of feces is designed to effectively contain and process BM. The first and second absorbent assemblies may comprise absorbent cores which are very similar in size and shape, or the absorbent cores may be different sizes or shapes and may include different materials. Further, each absorbent assembly may include additional elements such as topsheets, backsheets, acquisition zones, barriers, etc.

Figure 3:
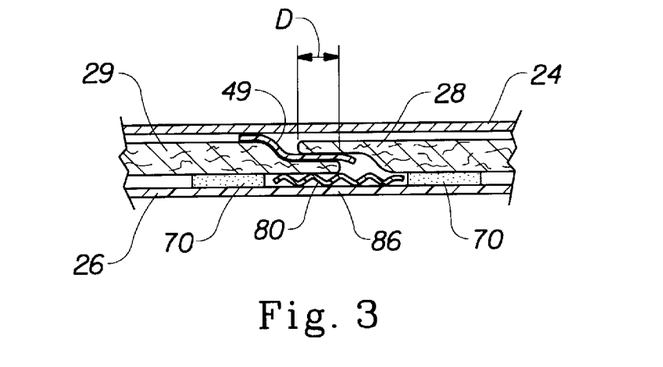
FIG. 3 is an enlarged fragmentary cross-sectional view of an alternative embodiment of the invention.
Figure 10:
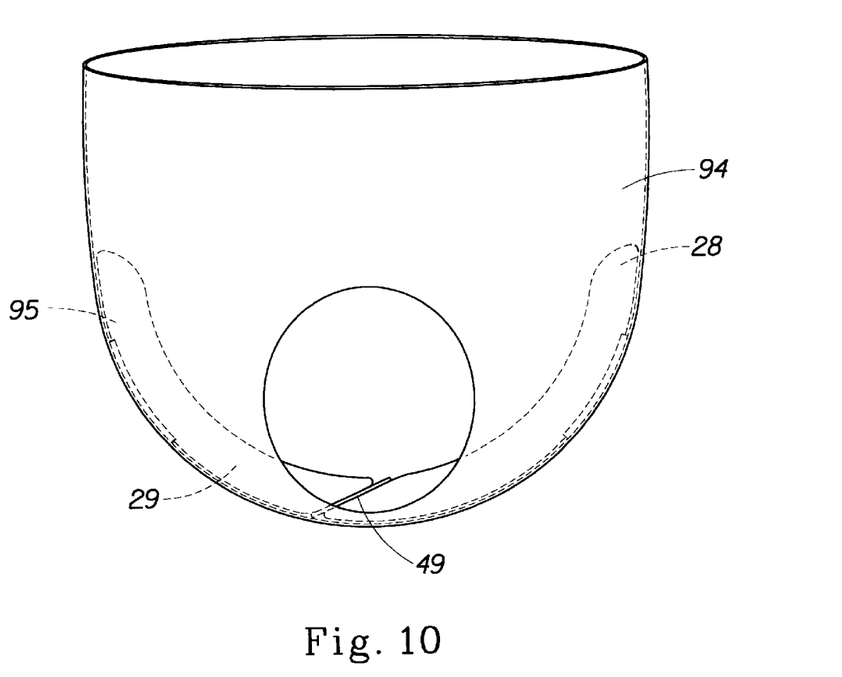
FIG. 10 is a side view of one embodiment of the present invention shown as it would be configured when on a wearer.

The first and second absorbent assemblies 28 and 29 may be spaced apart longitudinally, may abut one another, or may have portions which overlap (as shown in FIGS. 3 and 10). (As used herein, the term "spaced apart longitudinally" refers to a relative spacing between elements wherein the elements are spaced apart in a direction preferably parallel with the longitudinal centerline 100 of the diaper 20.) The longitudinal spacing between the first absorbent assembly 28 and the second absorbent assembly 29 is approximated by the letter D, as shown in FIG. 2. The spacing D between the absorbent assemblies 28 and 29 may be adjusted and readjusted by the caretaker in order to provide the best fit and containment characteristics for the particular wearer at any particular time during use. For example, the first absorbent assembly 28 may be adjusted so as to be in an ideal location for absorbing and containing urine and the second absorbent assembly 29 may be adjusted to be in an ideal location for absorbing and/or containing BM.

In one preferred embodiment, the spacing D between the absorbent assemblies may be adjusted anywhere from at least about −1 cm (overlapping) to about 1 cm for average medium size babies (between about 12 and about 25 pounds). Adult incontinence garments, however, may have much larger ranges for the spacing of the absorbent assemblies due to their generally larger chassis. (For example, incontinence garments may have spacing between the absorbent assemblies anywhere from at least about −20 cm to about 20 cm.) More preferably, the spacing D between the first absorbent assembly 28 and the second absorbent assembly 29 may be adjusted from at least about −5 cm to about 5 cm, or between at least about −10 cm and about 10 cm. Of course, the first absorbent assembly 28 may be positioned to abut the second absorbent assembly 29 such that the spacing D would be adjustable from 0 cm to anywhere between about −10 cm to about 10 cm or anywhere between about 20 cm or 20 cm. Thus, the ranges of spacing may be varied depending on the intended use and may include embodiments where the spacing ranges from abutting to a positive spacing or from abutting to an overlapping spacing. Other embodiments may be adjustable only in positive spacing ranges (i.e., the assemblies are always spaced apart) or adjustable only in negative spacing ranges (i.e., the assemblies are always at least partially overlapping).

With reference to FIGS. 1, 4 and 5–7 the diaper 20 preferably comprises a first absorbent assembly 28 generally located toward the front of the diaper 20, a second absorbent assembly 29 located toward the rear of the diaper 20, and a adjustment member 80 joined or operatively associated with both the first absorbent assembly 28 and the second absorbent assembly 29.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference. An exemplary embodiment of a suitable absorbent structure is disclosed in U.S. Pat. No. 5,137,537 issued to Herron et al.

The adjustment member 80 which generally joins the absorbent assemblies 28 and 29, directly or indirectly, provides a means for adjusting the relative spacing and orientation of the first and second absorbent assemblies 28 and 29. (In some preferred embodiments, the adjustment member 80 may be joined to either the first absorbent assembly 28 or the second absorbent assembly 29. However, the adjustment member 80 may be joined to the topsheet 24, the backsheet 26, both the topsheet 24 and the backsheet 26 or any other element of the diaper 20.) The adjustment member 80 provides the caretaker with the ability to achieve improved relative longitudinal positioning of the urine and feces collection zones 90 and 92 based on the anatomy of the specific wearer. (The term "longitudinally positioning" as used herein refers to the location of a specific element or elements along the longitudinal centerline 100 of the diaper 20 or along another similarly situated, generally parallel axis.) Additionally, the adjustment member 80 may provide the caretaker with the ability to change the fit and overall length of the diaper 20 without losing the correct relative positioning of the urine and feces collection zones 90 and 92. As mentioned above, this is beneficial due to the significant variation in specific dimensions between humans having the same general size and weight. For infants especially, the ability to change the size of the diaper 20 and the orientation of the urine collection zone 90 and the feces collection zone 92 relative to one another is important due to their rapidly changing body size and weight as well as the quite extreme differences between babies of the same age.

In preferred embodiments, the adjustment member 80 provides for "continuous adjustment" throughout a particular range. (As used herein, the term "continuous adjustment" refers to the ability of elements of the diaper to be positioned relative to each other in an infinite number of "settings" or configurations along a predetermined path or paths.) For example, the adjustment member 80 may provide an infinite number of configurations with different spacings (or overlap) between the absorbent assemblies within a certain range (e.g. −20 cm to 20 cm). Alternatively, the adjustment member 80 may have a defined number of "settings" or positions to which it can be intermittently adjusted. An example of this type of intermittent would be an adjustment member which has only two settings or positions, such as where the absorbent assemblies are either abutting or are spaced apart a predetermined distance. It is generally preferred to increase the caretaker's flexibility by increasing the number of available settings of positions to which the diaper can be adjusted.

The adjustment member 80 may be a single element or may include any number of separate or joined elements and may include absorbent or non-absorbent materials. As used herein, the term "absorbent" refers to materials which receive and contain body fluids. The term "non-absorbent" refers to materials which do not receive and contain body fluids, but rather tend to be hydrophobic and/or allow fluids to pass through them without containing them.

The adjustment member 80 may have elastic, inelastic, or reversible inelastic extension properties, or a combination of the above. As used herein, the terms "elastic", "elastically extensible" and "elastomeric" refer to elements which, if extended maintain a return force that tends to return the element to substantially its original dimensions and configuration. Preferred elastic adjustment members 80 may comprise any elastic, elastomer or elastically extensible material known in the art, including but not limited to elastomeric strands, films, nonwoven materials woven materials, laminates, scrims, springs, foams, adhesives, and the like, or any combination thereof.

The adjustment member 80 may comprise all or a portion of the backsheet 26. In one preferred embodiment, as shown in FIG. 3, the backsheet 26 includes at least a portion 86 which is elastically extensible. The elastically extensible portion 86 is preferably at least partially located longitudinally inboard of the attachment means 70 joining the absorbent assemblies to the backsheet 26. The extensible portion 86 of the backsheet 26 may be the adjustment member 80 or may be one element in a multiple element adjustment member 80.

In embodiments wherein, the adjustment member 80 is relatively "inelastic", little or no return force is generated when the adjustment member 80 is subjected to an elongation or contractive force. Thus, the adjustment member 80 does not tend to want to return to its original dimensions or configuration when the force is removed, but rather tends to maintain its new shape or configuration. In one embodiment, the first and second absorbent assemblies 28 and 29 may be joined by an inelastically extensible material, such as a carded polypropylene nonwoven designated P-8 or P-11 from Veratec Nonwoven Group of the International Paper Company of Walpole, Mass. or any other inextensible material that can be adjusted to configure the absorbent assemblies.

The inelastic adjustment member 80 may be "reversible". As used herein the term "reversible" means the structure, once extended, contracted or adjusted, may be restored to substantially its original dimension or configuration upon the application of a force generally opposite to the force that resulted in the original extension, contraction or adjustment. In one embodiment, the adjustment member 80 comprises a thin relatively inelastic wire-like element which joins the first and second absorbent assemblies 28 and 29. (As used herein, the term "wire-like" is not meant to limit the materials which the adjustment member 80 may comprise, but rather is used to describe one embodiment of the invention having an adjustment member 80 which has a cross section relatively shorter than the overall length of the member.) In other embodiments, the adjustment member 80 may include an inelastic corrugated material, or the like, which may be extended or contracted.

Figure 4:
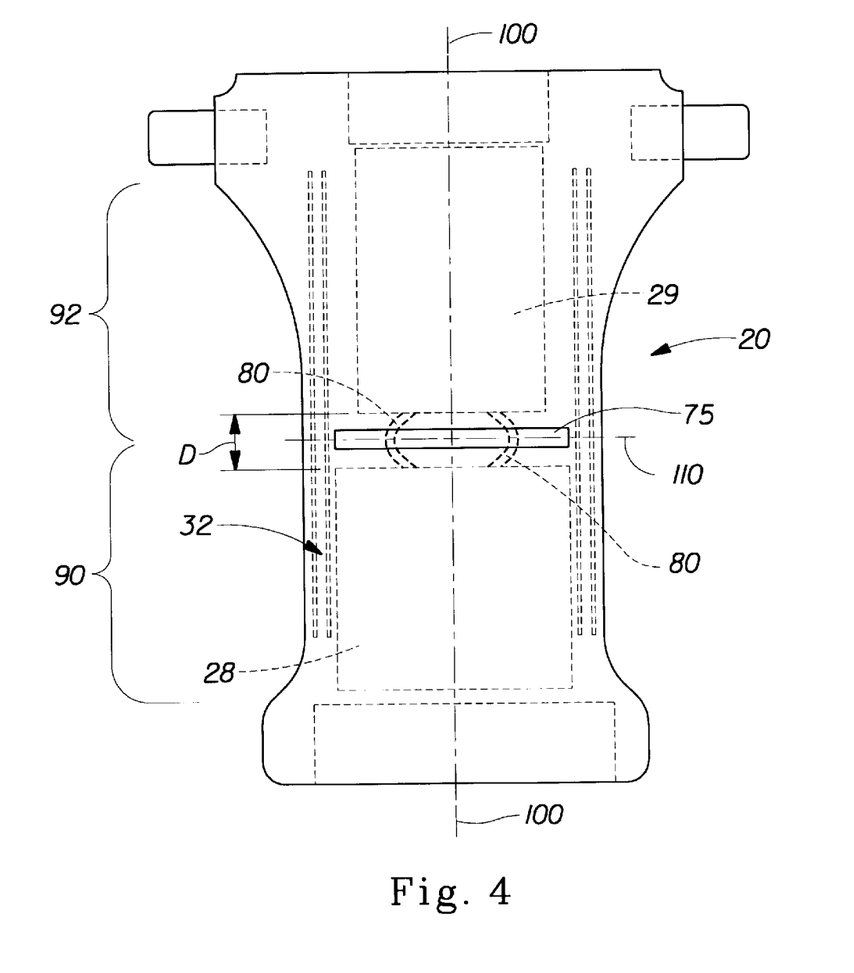
FIG. 4 is a plan view of an absorbent article embodiment of the present invention having portions cut away to reveal the underlying structure, the garment-facing surface of the diaper facing the viewer.
Figure 5:
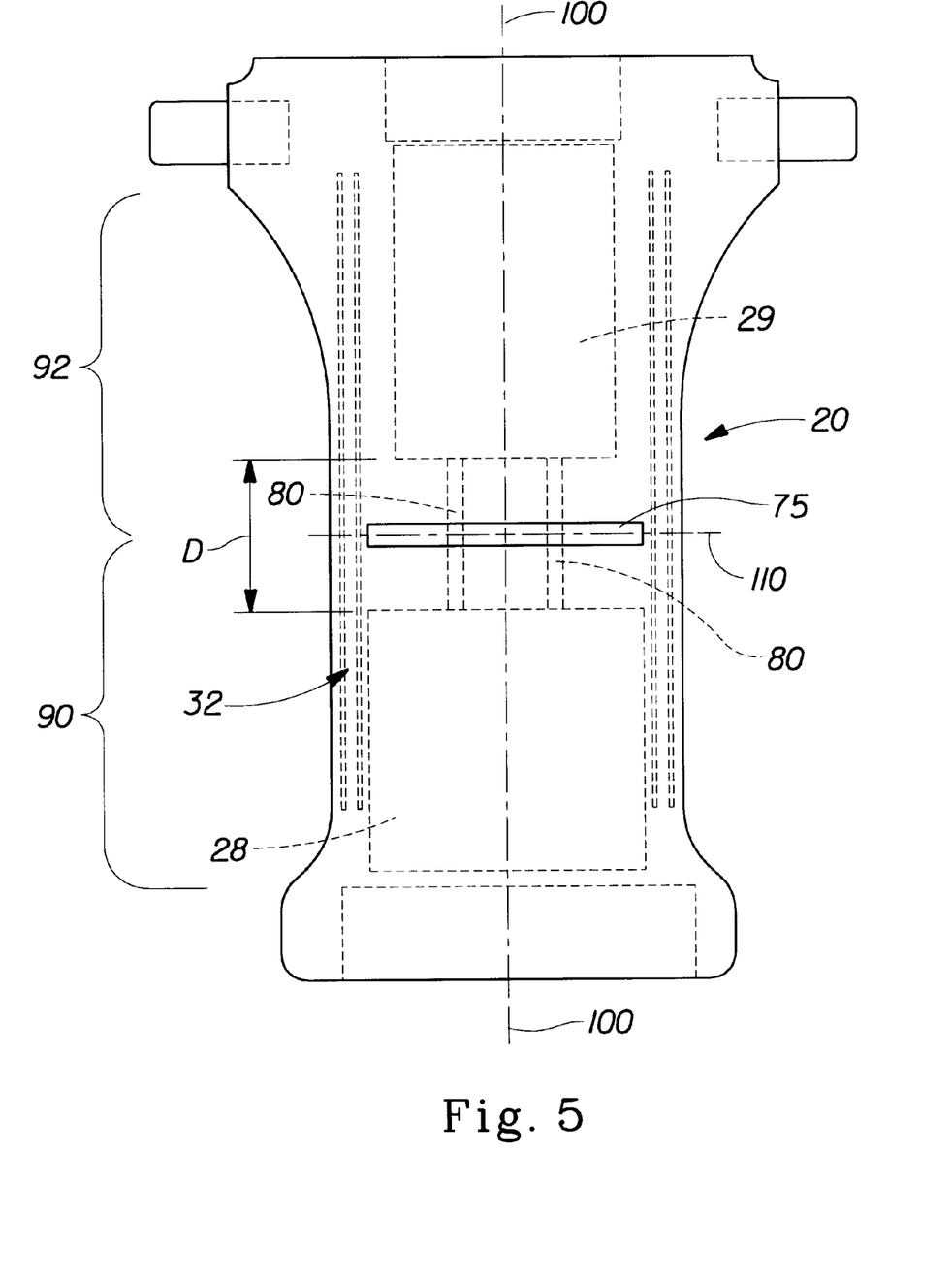
FIG. 5 is a plan view of an absorbent article embodiment of the present invention having portions cut away to reveal the underlying structure, the garment-facing surface of the diaper facing the viewer.

As shown in FIG. 5, the adjustment member 80 allows for the elongation of the diaper 20 and the separation of the first absorbent assembly 28 and the second absorbent assembly 29 upon the application of a tensile force generally in the longitudinal direction of the diaper 20. Another force generally along the same axis may result in restoration of the structure to its original configuration or to any other configuration limited only by the characteristics of the adjustment member 80 or any other element of the diaper 20. As shown in FIGS. 4 and 5, the adjustment member 80 may bend or deform in some way to provide the adjustment between the absorbent assemblies. However, alternative embodiments are contemplated wherein the adjustment member does not bend or deform.

Figure 6:
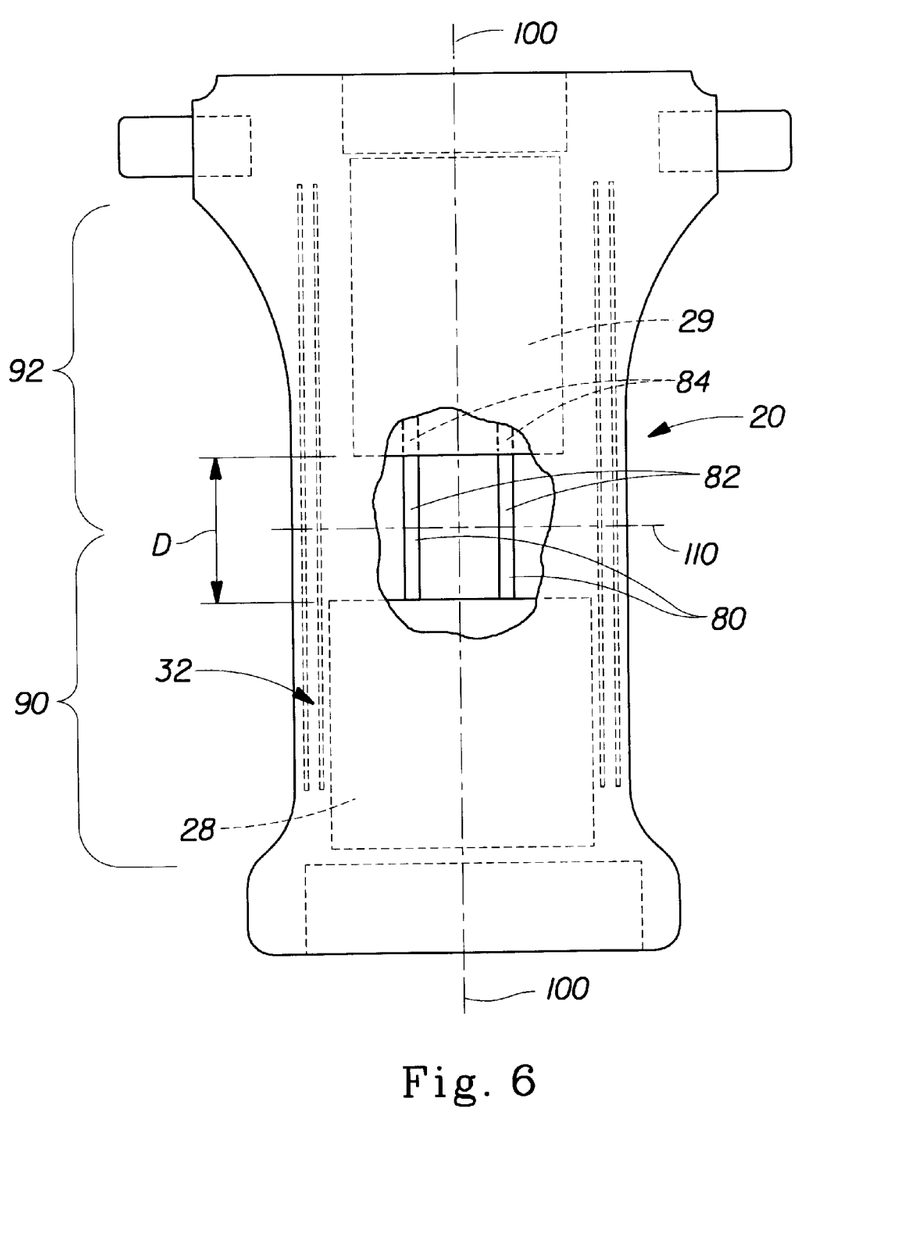
FIG. 6 is a plan view of an alternative embodiment of the present invention having portions cut away to reveal the underlying structure, the garment-facing surface of the diaper facing the viewer.
Figure 7:
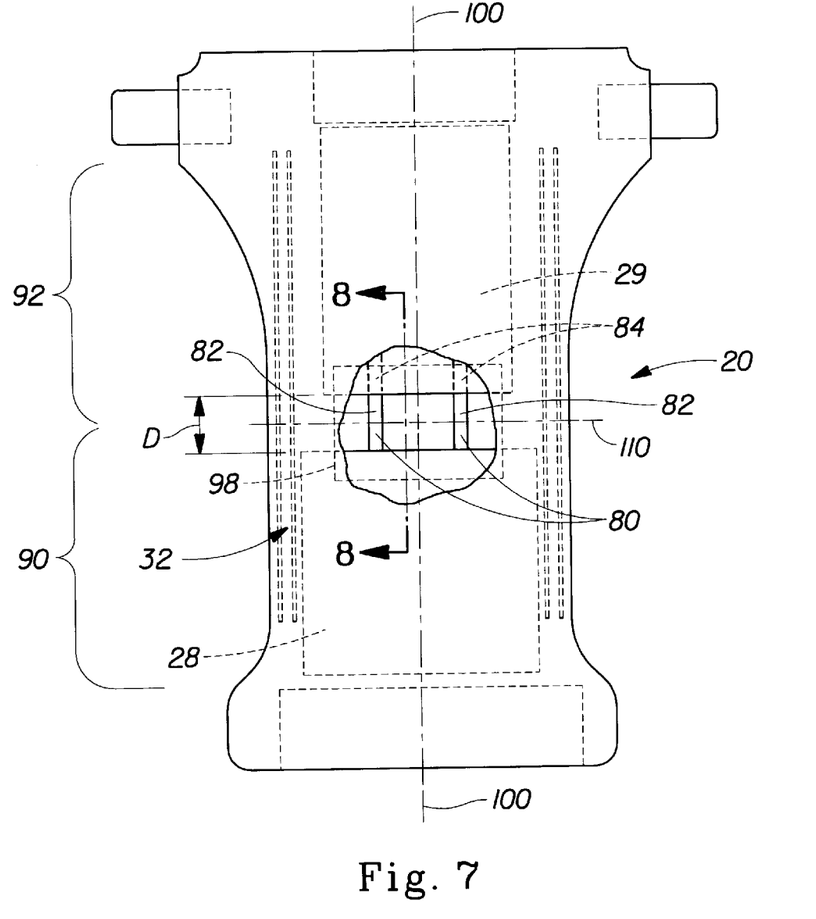
FIG. 7 is a plan view of an alternative embodiment of the present invention having portions cut away to reveal the underlying structure, the garment-facing surface of the diaper facing the viewer.

One exemplary embodiment of the present invention having an adjustment member 80 which is slideable and thus, does not necessarily deform to provide adjustment, is shown in FIGS. 6 and 7. (FIG. 6 shows the diaper 20 in a more extended configuration than that shown in FIG. 7.) The adjustment member 80 may be slideably joined with either the first absorbent assembly 28, the second absorbent assembly 29 or both. In a preferred embodiment, the adjustment member 80 includes at least one slideable member 82 which is aperturely associated with at least one of the absorbent assemblies. In other preferred embodiments, a chamber 84 is provided for the slideable member 82 to move within. Embodiments are also contemplated wherein the slideable member 82 does not slide into one of the absorbent assemblies or a chamber within the absorbent assembly, but rather slides within or along another element of the diaper.

The slideable member 82, the chamber 84 or any other operatively associated structure may include an element or elements for restricting the motion of the slideable member relative to the other structure. One nonlimiting example would be a slideable member having ridges which slide past complementary ridges or other suitable structure associated with the chamber 84 such that the absorbent assemblies 28 and 29 are intermittently adjustable over a larger range of adjustability. (As used herein, the term "intermittently adjustable" refers to the ability of elements to be positioned with respect to each other in such a way that certain predetermined settings or configurations can be obtained by the application of forces to portions of the product. This is in contrast to the infinite number of configurations available in continuously adjustable embodiments, as described above.)

In another preferred embodiment, the diaper 20 comprises urine and feces collection zones 90 and 92 overlapping each other and having one or more relatively low friction slip element 49 disposed between the zones. An example of a preferred slip element 49 comprises a plastic film such as the 1.0 mil polypropylene film designated 1401 manufactured by Clopay Corporation of Cincinnati, Ohio. Other slip elements may include webs, fibers, lotions, oil, foils, powder or any other material or structure capable of providing the function described herein. The slip element 49 preferably reduces the friction between the overlapping portions of the absorbent assemblies such that they may be adjusted relative to one another more easily. However, embodiments are contemplated wherein the slip element(s) 49 provide for reduced friction when the absorbent assemblies are adjusted in at least one direction and provides for greater friction when the absorbent assemblies are adjusted in another directions. Thus, the slip element 49 may be used to help maintain the configuration of the absorbent assemblies once they have been adjusted relative to one another. Since the friction between elements is generally material dependent, embodiments are contemplated wherein no slip element is required or even desired.

Figure 8:
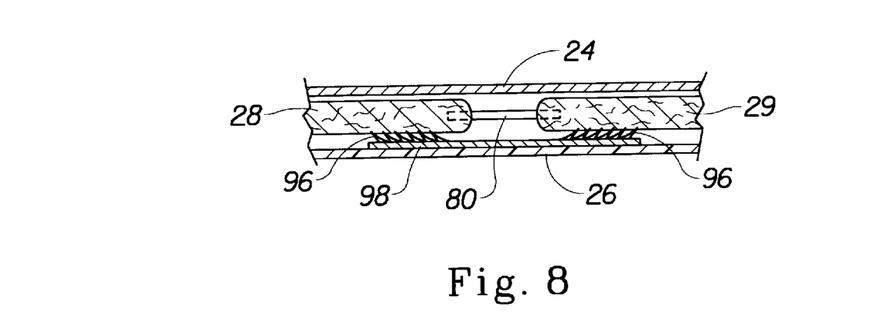
FIG. 8 is an enlarged fragmentary cross-sectional view taken along section line 8—8 of FIG. 7.

Any of the above described embodiments or any other embodiments within the scope of the of the inventions may also include an adjustment holding member 98 which fixes the absorbent assemblies 28 and 29 and/or urine and feces collection zones 90 and 92 in a particular relationship to each other. The holding member 98 may include any portion of one or more of the elements making up the diaper, absorbent assemblies, collection zones or adjustment member. For example, the holding member 98 may include a slip element 49 as described above which uses friction to hold the absorbent assemblies 28 and 29 in place after adjustment. Further, however, any other holding member may be used which is separate from the other elements of the diaper 20 and joined thereto. Suitable holding members 98 include adhesives; mechanical fasteners; belts; buckles; pins; ties; magnetics; electronics; teeth or any combination of these or other known fastening and/or holding devices. The holding member 98 may also be disposed on the outer surface of the diaper 20 and between any other elements. In one embodiment, as shown in FIG. 8, the holding device 98 includes teeth 96 which hold the absorbent assemblies 28 and 29 apart once they have been positioned. (As used herein, the term "teeth" includes any single structure or multiple structure which extend from the holding member.) The teeth may extend perpendicularly from the base of the holding device 98 or may be at any angle. The teeth may also have any suitable length, shape or hardness, etc.

The diaper 20 may also comprise an upstanding transverse barrier 75, as shown in FIGS. 4 and 5, that prevents exudates from migrating from the rear waist region 38 to the front waist region 36 of the diaper 20, or vice versa. The transverse barrier 75 is preferably joined to the chassis 22 and located adjacent the longitudinal centerline 100, although other configurations are contemplated. Other examples of suitable transverse barriers are described in U.S. application Ser. No. 08/347,026 entitled "Absorbent Article Having Multiple Effective Height Transverse Partition" filed Nov. 30, 1994 in the name of Dreier et al.; and in PCT Patent WO 94/14395 entitled "Absorbent Article Having An Upstanding Transverse Partition" published Jul. 7, 1994 in the name of Freeland, et al. Both of the above-cited references are hereby incorporated by reference herein.

The diaper 20 is preferably applied to a wearer by positioning one of the waist regions, preferably the rear waist region 38, under the wearer's back and drawing the remainder of the diaper 20 between the wearer's legs. The other waist region, preferably the front waist region 36, is positioned across the front of the wearer. The diaperer then wraps the side panels 30 around the wearer such that the front waist region 36 and the rear waist region 38 are in an overlapping configuration. The side panels 30 will typically be extended and tensioned during this operation so as to conform to the size and shape of the wearer. The fastening system is secured to effect a side closure.

Figure 9:
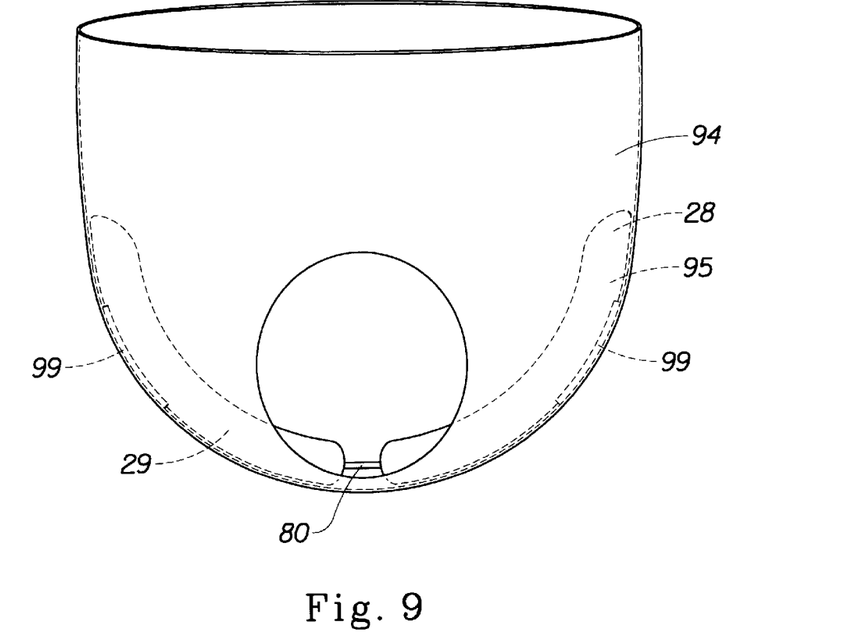
FIG. 9 is a side view of one embodiment of the present invention shown as it would be configured when on a wearer.

In another embodiment, the absorbent article of the present invention may be an insert 95 which is intended to be placed in the wearer's underwear, an outer cover 94 or the like. Thus, the insert 95 is generally not intended to take the form of a pant, but rather is to be used in conjunction with a pant or other structure which holds the insert 95 in place about the wearer. An example of an insert 95 disposed in an outer cover 94 is shown in FIG. 9. The absorbent insert 95 includes a first absorbent assembly 28 and a second absorbent assembly 29. The first and second absorbent assemblies are joined, directly or indirectly, by at least one adjustment member 80. The adjustment member(s) 80 may include any one or more of the adjustment member structures hereinbefore described. Further, the absorbent assemblies 28 and 29 may be positioned in any of the configurations described above, such as overlapping or separated. The absorbent insert 95 may also include one or more attachment element(s) 99 to hold the insert 95 in place in the pant or outer cover 94 during use. The attachment element 99 may comprise adhesive, cohesive, hooks, snaps, buckles, buttons, ties, magnetic, electronic and/or any other know means for attaching absorbent articles to undergarments.

In another preferred embodiment, the insert 95 comprises absorbent assemblies 28, 29 at least partially overlapping each other. The insert 95 preferably includes one or more slip element(s) 49 disposed between the overlapping portions of the absorbent assemblies. The slip element 49 preferably reduces the friction between the overlapping portions of the absorbent assemblies such that they may be adjusted relative to one another more easily. However, embodiments are contemplated wherein the slip element(s) 49 provide for reduced friction when the absorbent assemblies are adjusted in at least one direction and provides for greater friction when the absorbent assemblies are adjusted in another directions. Thus, the slip element 49 may be used to help maintain the configuration of the absorbent assemblies once they have been adjusted relative to one another. An example of a preferred slip element 49 comprises a plastic film such as the 1.0 mil polypropylene film designated 1401 manufactured by Clopay Corporation of Cincinnati, Ohio. Other slip elements may include webs, fibers, lotions, oil, foils, powder or any other material or structure capable of providing the function described herein.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent insert for use with an outer cover, the outer cover having a front waist region, a rear waist region, a longitudinal centerline and a lateral centerline perpendicular to said longitudinal centerline, the absorbent insert comprising:
   a first absorbent assembly;
   a second absorbent assembly; and
   an adjustment member adjustably joining said first absorbent assembly and said second absorbent assembly such that said first absorbent assembly and said second absorbent assembly are moveable relative to each other in at least a direction parallel to said longitudinal centerline; and
   a slip element joined with at least a portion of the first absorbent assembly, said slip element providing a low friction surface such that at least a portion of said first absorbent assembly can be positioned over at least a portion of said second absorbent assembly in an overlapping configuration.

2. The absorbent insert of claim 1 wherein the adjustment member is non-absorbent. absorbent.

3. The absorbent insert of claim 1 wherein said slip element provides reduced friction between said first absorbent assembly and said second absorbent assembly when said absorbent assemblies are adjusted relative to each other in a first direction and said slip element provides increased friction between said first absorbent assembly and said second absorbent assembly when said absorbent assemblies are adjusted relative to each other in a second direction.

4. An absorbent insert for use with an outer cover, the outer cover having a front waist region, a rear waist region, a longitudinal centerline and a lateral centerline perpendicular to said longitudinal centerline, the absorbent insert comprising:

a first absorbent assembly;

a second absorbent assembly; and an inelastically adjustable adjustment member adjustably joining said first absorbent assembly and said second absorbent assembly such that said first absorbent assembly and said second absorbent assembly are moveable relative to each other in at least a direction parallel to said longitudinal centerline, of said outer cover when said insert is disposed in said outer cover, said adjustment member having a length and a cross section, said cross section being shorter than said length; and a slip element joined with at least a portion of the first absorbent assembly, said slip element providing a low friction surface such that at least a portion of said first absorbent assembly can be positioned over at least a portion of said second absorbent assembly in an overlapping configuration.

5. The absorbent insert of claim 4 wherein the adjustment member is non-absorbent.

6. The absorbent insert of claim 4 wherein said slip element provides reduced friction between said first absorbent assembly and said second absorbent assembly when said absorbent assemblies are adjusted relative to each other in a first direction and said slip element provides increased friction between said first absorbent assembly and said second absorbent assembly when said absorbent assemblies are adjusted relative to each other in a second direction.

7. An absorbent insert for use with an outer cover, the outer cover having a front waist region, a rear waist region, a longitudinal centerline and a lateral centerline perpendicular to said longitudinal centerline, the absorbent article comprising:

a first absorbent assembly;

a second absorbent assembly; and a slideable adjustment member slideably joining said first absorbent assembly and said second absorbent assembly such that said first absorbent assembly and said second absorbent assembly are adjustable relative to each other in at least a direction parallel to said longitudinal centerline of said outer cover when said insert is disposed in said outer cover; and a slip element joined with at least a portion of the first absorbent assembly, said slip element providing a low friction surface such that at least a portion of said first absorbent assembly can be positioned over at least a portion of said second absorbent assembly in an overlapping configuration.

8. The absorbent insert of claim 5 wherein said slideable adjustment member is slideably joined to a chamber formed in at least one of said first or said second absorbent assemblies.

9. The absorbent insert of claim 7 wherein said slideable adjustment member is slideably joined to a chamber formed in both said first and said second absorbent assemblies.

10. The absorbent insert of claim 7 wherein said slideable adjustment member includes a restricting element which restricts the movement of the adjustment member to provide for intermittent adjustability.

11. The absorbent insert of claim 10 wherein said restricting element includes ridges on said slideable adjustment member.

12. The absorbent insert of claim 11 wherein said restricting element includes ridges disposed in said chamber which engage ridges on said slideable adjustment member to provide for intermittent adjustability.

13. The absorbent insert of claim 7 wherein said slip element provides reduced friction between said first absorbent assembly and said second absorbent assembly when said absorbent assemblies are adjusted relative to each other in a first direction and said slip element provides increased friction between said first absorbent assembly and said second absorbent assembly when said absorbent assemblies are adjusted relative to each other in a second direction.

* * * * *

UNITED STATES PATENT AND TRADEMARK OFFICE
CERTIFICATE OF CORRECTION

PATENT NO. : 6,090,090
DATED : July 18, 2000
INVENTOR(S) : Donald C. Roe et al.

It is certified that error appears in the above-identified patent and that said Letters Patent is hereby corrected as shown below:

Column 14, line 57, "non-absorbent. absorbent" should read --non-absorbent--.

Signed and Sealed this

Seventeenth Day of April, 2001

*Attest:*

NICHOLAS P. GODICI

*Attesting Officer*     *Acting Director of the United States Patent and Trademark Office*